(12) United States Patent (10) Patent No.: US 7,785,106 B2
Takahashi (45) Date of Patent: Aug. 31, 2010

(54) SPONGE PROPHY

(76) Inventor: Atsushi Takahashi, 20-15-1, Kizaki, Tsuruga-Shi, Fukul 914-0814 (JP)

( * ) Notice: Subject to any disclaimer, the term of this patent is extended or adjusted under 35 U.S.C. 154(b) by 314 days.

(21) Appl. No.: 10/524,991

(22) PCT Filed: Aug. 20, 2003

(86) PCT No.: PCT/JP03/10477

§ 371 (c)(1),
(2), (4) Date: Feb. 23, 2006

(87) PCT Pub. No.: WO2004/017855

PCT Pub. Date: Mar. 4, 2004

(65) Prior Publication Data

US 2006/0166166 A1 Jul. 27, 2006

(30) Foreign Application Priority Data

Aug. 20, 2002 (JP) .............................. 2002-238994

(51) Int. Cl.
*A61C 3/06* (2006.01)
(52) U.S. Cl. .................. 433/166; 433/125; 433/142
(58) Field of Classification Search ................. 433/166, 433/125, 51, 142; 15/244.1, 97.1, 97.2, 101, 15/230, 230.18, 230.19, 231; 401/42
See application file for complete search history.

(56) References Cited

U.S. PATENT DOCUMENTS

| | | | | |
|---|---|---|---|---|
| 809,615 A * | 1/1906 | Hopkins | ...................... | 15/231 |
| 1,218,081 A * | 3/1917 | Hahn | ........................ | 401/203 |
| 1,617,838 A * | 2/1927 | Fennell | .................... | 15/230.18 |
| 1,820,256 A * | 8/1931 | Stewart | ...................... | 15/244.3 |
| 2,265,804 A * | 12/1941 | Deady | ........................ | 401/203 |
| 2,364,205 A * | 12/1944 | Fuller | ......................... | 601/141 |
| 2,456,782 A * | 12/1948 | Hartman | ..................... | 15/231 |
| 2,779,962 A * | 2/1957 | Cooper | ........................ | 401/42 |
| 2,789,352 A * | 4/1957 | Wiseman | .................... | 433/166 |
| 2,804,728 A * | 9/1957 | Politzer et al. | ............. | 451/532 |
| 2,940,102 A * | 6/1960 | Marinus | ........................ | 401/6 |
| 3,142,138 A * | 7/1964 | Kean et al. | ................... | 451/541 |
| 3,243,925 A * | 4/1966 | Buzzell | ....................... | 451/504 |
| 3,911,922 A * | 10/1975 | Kliger | ......................... | 604/362 |
| 4,008,189 A * | 2/1977 | VAN Leuwen et al. | ...... | 521/174 |
| 4,831,676 A * | 5/1989 | Denmark | ................. | 15/104.93 |
| 5,052,840 A * | 10/1991 | St. Cyer | ..................... | 401/201 |
| 5,078,754 A * | 1/1992 | Jefferies et al. | ............... | 51/298 |
| 5,273,558 A * | 12/1993 | Nelson et al. | ................. | 51/298 |
| 6,254,468 B1 * | 7/2001 | Gozzi et al. | ................. | 451/526 |

FOREIGN PATENT DOCUMENTS

EP 1508586 A1 * 2/2005
JP 2002053469 A * 2/2002

* cited by examiner

*Primary Examiner*—Cris L Rodriguez
*Assistant Examiner*—Hao D Mai

(57) ABSTRACT

A dental prophy chip with a hollow core of different shapes such as canopy, cylinder, cup and inverted cone, is covered by hydrophilic grindstone sponge containing a polishing agent and its edge is either pressed fixed or folded into the interior of the core with a latch plate. A shaft is fixed to the latch plate to avoid resonance at bottom surface, during rotation. The device maintains polishing efficiency by avoiding transverse oscillation in polishing barrel-shaped tooth clearance and reducing frictional heat.

10 Claims, 5 Drawing Sheets

SPONGE PROPHY

BACKGROUND

The invention relates to hydrophilic sponge processing, and a cleaning, polishing, and burnishing prophy chip utilizing a hydrophilic sponge.

Generally, conventional dental cleaning is performed with a prophy chip (cup), mounted on a dental instrument, composed of silicon gum with a dental polishing gel or paste, or the polishing paste may be directly applied to appliances to clean, polish, or burnish the teeth. However, the top of the prophy chip may be twisted or frayed when polishing the embrasure or its adjacent side, and the prophy cup cannot reach the target sites.

In addition, polishing gel or paste may escape the oral cavity due to rotation when cleaning teeth with the prophy chip composed of silicon gum. The supplement of the polishing gel or paste for preventing heat generated by friction between the silicon gum and teeth and maintaining polishing efficiency is required, and this also interrupts the operation.

To solve these problems, a polishing grindstone sponge requiring no polishing paste maybe applied, and the drawbacks of the silicon gum during polishing do not occur.

The invention provides a prophy chip for cleaning, polishing, and burnishing teeth reducing heat generated by friction without requiring a polishing paste.

SUMMARY

A prophy chip is provided, mounted on the top of a dental rotary instrument, comprising a hollow cup-shaped core of canopy (semispherical) type, cylindrical type, cup type, cone type, inverted cone type or disk type, covered with a hydrophilic grindstone sponge containing a polishing agent such as aluminum oxide, silicon carbide, cerium oxide, or pumice, the hydrophilic grindstone sponge side edge either being press fixed by folding into the interior of the core with a shank-equipped latch plate or contoured for gripping, a shaft fixed to avoid vibration around the latch plate bottom surface rotation axis during rotation.

With the prophy chip of the invention, the contact side of the sponge which lines the core may be deformed to the core shape during cleaning and polishing. For example, the top of the cone-type core reaches embrasures without twisting, and the flexible surface of the sponge provides even contact and cleaning to the polishing face of the tooth. In another example, the prophy chip of the invention, even with the conventional inflexible silicon gum, still prevents the deformation of the top of the core. In practice, the indisposition by the lash of the friction between the stiff chip and the teeth can be reduced and the teeth cleaning and polishing can be properly operated by the flexible sponge.

Moreover, the cleaning, polishing, and burnishing can be operated by the hydrophilic sponge of the invention with abundant water, providing more effective dissipation of heat generated by friction.

Furthermore, solid agents in the hydrophilic sponge may dissolve and be released to the polishing face by centrifugal force, rolling friction, and pressure. Medicaments, polishing agents, or coating agents contained in the sponge may be dissolved and released to the contact face between the tooth and the rotating polishing chip. Sweeteners and fragrances can be diffused in the oral cavity during cleaning, polishing, and burnishing by a mediator such as saliva, providing refreshment and aromatherapeutic effects.

In particular, the prophy chip of the invention, mounted on the rotary dental instrument, capable of polishing difficult areas such as the embrasure or its adjacent side. In addition, polishing paste is not required during the operation, such that interruption of the procedure caused by the application of polishing paste in conventional operation does not occur. The disposition on the surfaces of treated teeth by friction between the stiff chip and the teeth can be reduced and teeth cleaning and polishing can be properly operated using the flexible sponge immersed in water prior to the operation, reducing heat generated by friction.

In addition, the hydrophilic sponge of the invention comprises at least one water soluble agent such as a polishing agent, a foaming agent, a medicament for inhibiting or preventing periodontal diseases or dental caries, or a coating agent. These agents can be dissolved and released to the surfaces of teeth or the entire oral cavity by water or saliva during cleaning, polishing, and burnishing for caries prevention, dental coating, as well as refreshment and aromatherapeutic effects.

Additionally, the hollow core of the invention may be filled with a water-retaining material, providing dissipation of heat generated by friction, also prolonging the effect of the medicaments.

BRIEF DESCRIPTION OF THE DRAWINGS

The invention can be more fully understood and further advantages become apparent when reference is made to the following description and the accompanying drawings in which.

SYMBOL LEGENDS

1~core; 2~hydrophilic grindstone sponge; 3~latch plate; 4~axis; 5~connection of axis and dental rotary instrument; 6~tooth (teeth); 7~hydrophilic grindstone sponge deformed by pressing; 8~pore; 10~grip of the body of the dental rotary instrument; 11~head of the dental rotary instrument; 12~switch of the dental rotary instrument; and 13~sponge prophy.

DETAILED DESCRIPTION

Practical embodiments of the invention are described herein in accordance with the figures.

Figure 1:
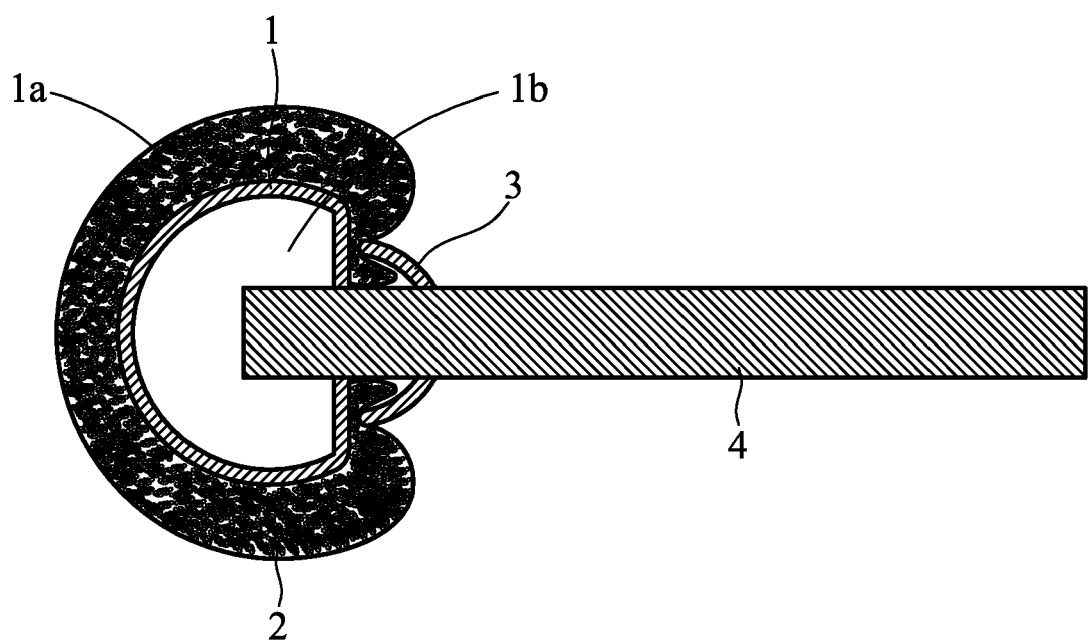
FIG. 1 is a cross-section of a spherical sponge prophy in one embodiment of the invention.
Figure 2:
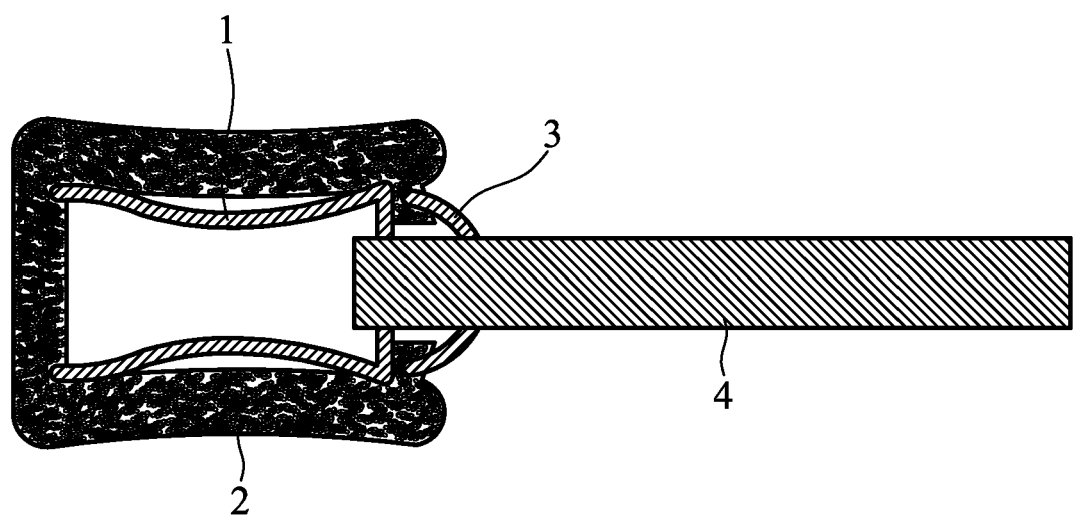
FIG. 2 is a cross-section of a cylindrical sponge prophy in another embodiment of the invention.
Figure 3:
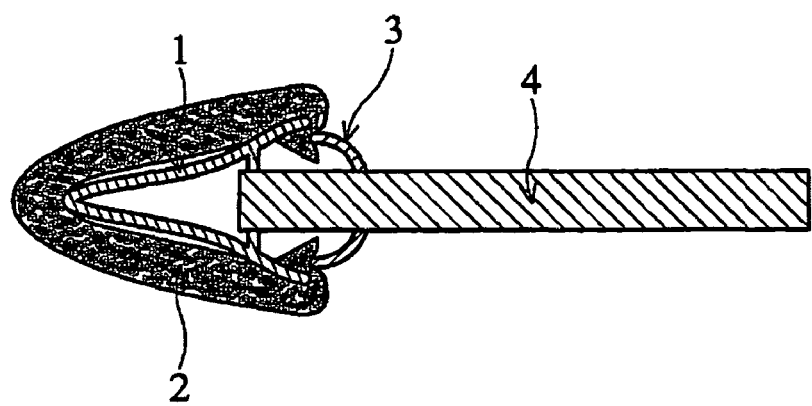
FIG. 3 is a cross-section of a conical sponge prophy in another embodiment of the invention.

FIGS. 1~3 show embodiments of the invention, wherein like symbols indicate identical elements, showing basic components of the dental rotary instrument (or prophy sponge), with elements the same as the conventional dental rotary instruments omitted. The invention features replacement of the conventional chip composed of silicon gum with a hydrophilic grindstone sponge, as shown in FIG. 1.

The processing of these figures is further illustrated below.

Figure 8:
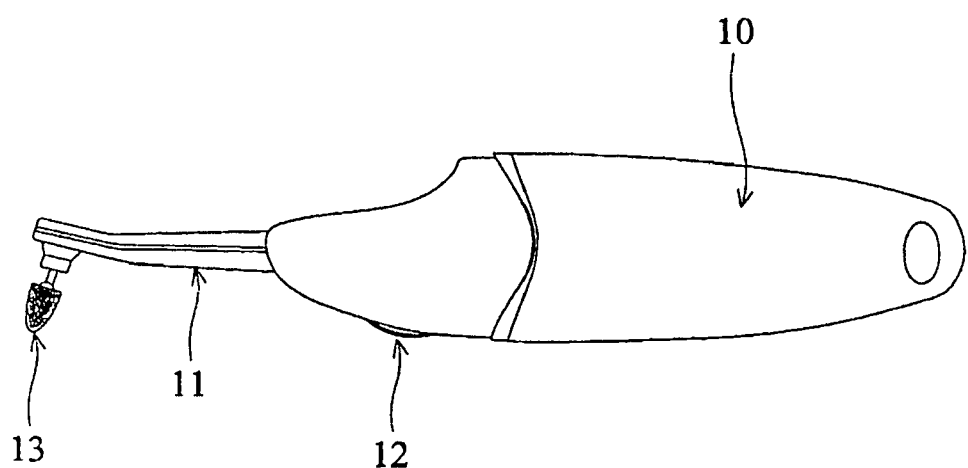
FIG. 8 is a lateral view of a dental rotary instrument equipped with a sponge prophy in one embodiment of the invention.

The sponge prophy as shown in FIGS. 1~3 is mounted on the dental rotary instrument as shown in FIG. 8. The hydrophilic sponge can be hydrophilic latex sponge, or polyurethane sponge, and the hydrophilic latex sponge or the hydrophilic polyurethane sponge comprises a grindstone of $Ca_{10}(PO_4)_6(OH)_2$ or $Ca_{10}(PO_4)_6F_2$ as a wet grindstone sponge. The core 1 comprises an exterior wall 1a and a hollow interior region 1b. The outside of the core is nonwoven to maintain the grindstone and has hydrophilicity and flexibility. The outside of the sponge covering the core is a three-dimensionally continuous, porous film conducting a solution immersing in a flexible polishing agent. Sponge prophy 13 contacts the surface of the tooth, and the switch 12 of the dental rotary instrument is turned on. Sponge prophy 13 is immersed in water prior to the operation and agents such as various medicaments, sweeteners, fragrances, dental coatings are dissolved on the contact surfaces between the teeth and the operating polishing chip, providing prevention periodontal diseases and dental caries, aromatherapy and refreshment effects, efficiency of cleaning, polishing, and burnishing, and inhibition of heat generated by friction.

Figure 4:
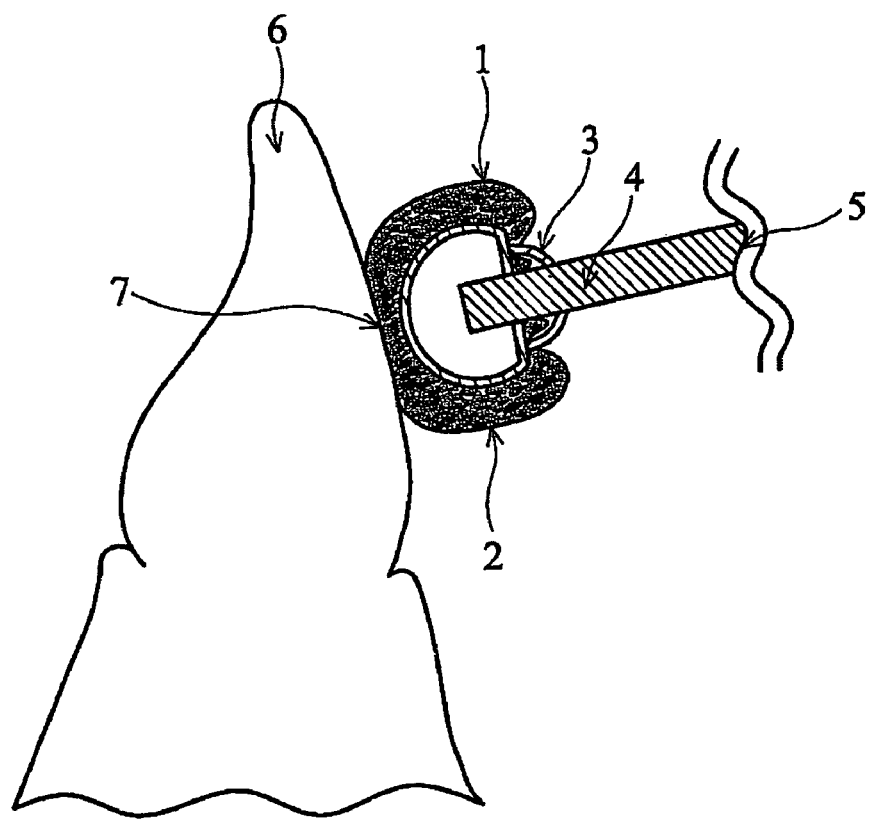
FIG. 4 is a cross-section of the spherical sponge prophy contacting a surface of a tooth and the hydrophilic grindstone sponge deforming accordingly.
Figure 5:
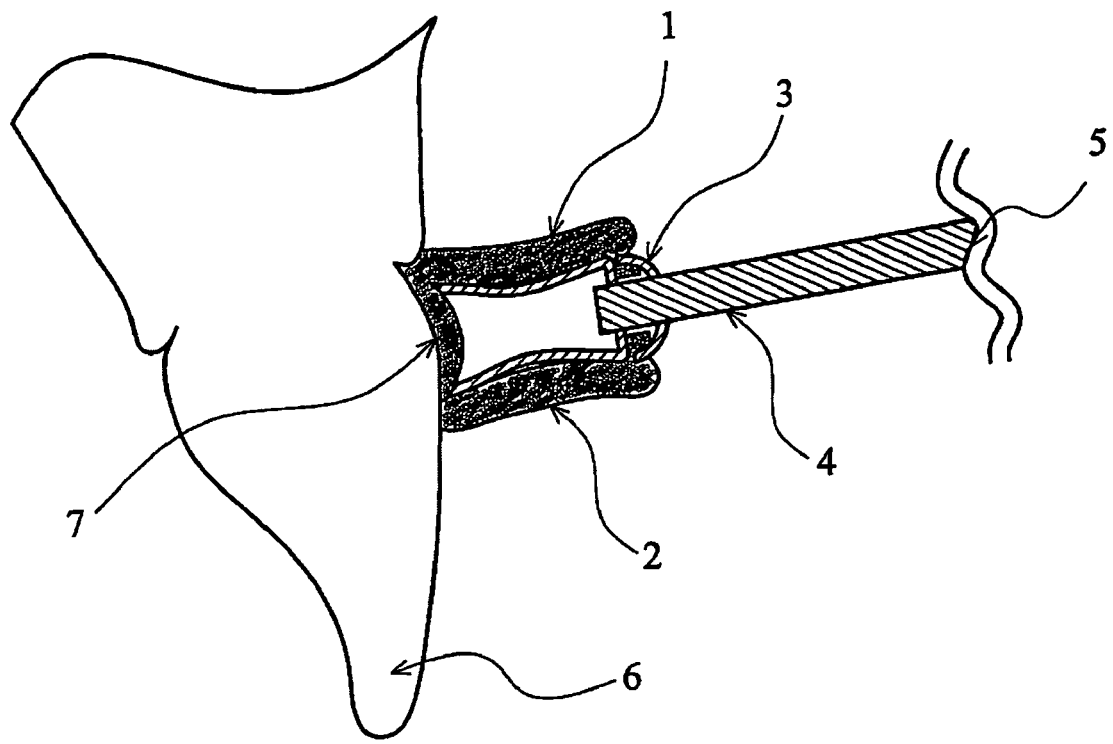
FIG. 5 is a cross-section of the cylindrical sponge prophy contacting a neck of a tooth and the hydrophilic grindstone sponge deforming accordingly.
Figure 6:
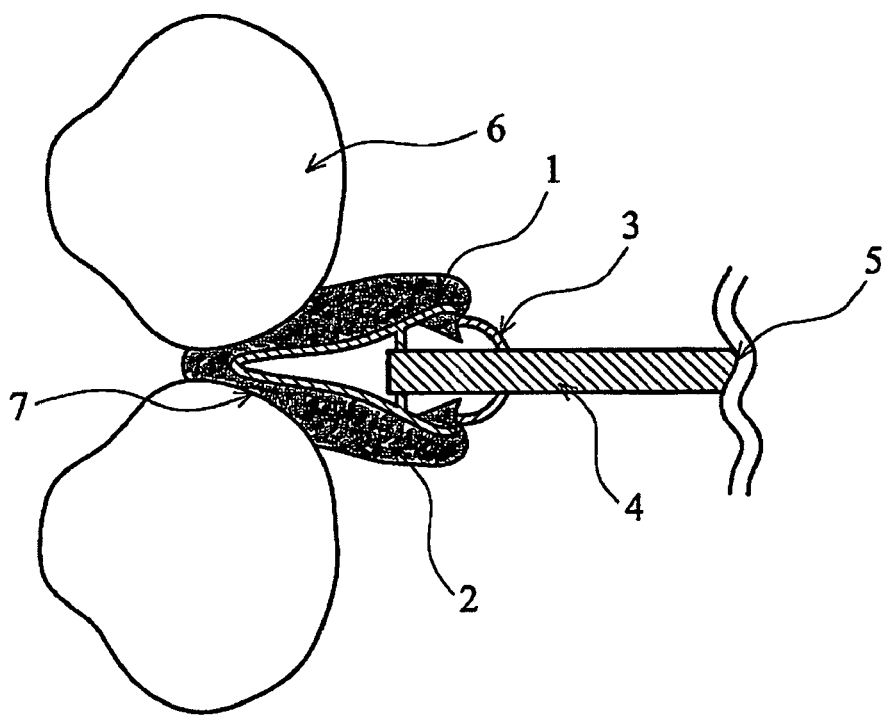
FIG. 6 is a cross-section of the conical sponge prophy contacting an embrasure and the hydrophilic grindstone sponge deforming accordingly.

In the embodiment of cleaning the surface of a tooth, the spherical sponge prophy as shown in FIG. 1 is applied to cleaning concaves such as the facies labialis dentis and the tongue side fossa as shown in FIG. 4. In the embodiment cleaning the neck of a tooth, the cup-shaped core covered with a hydrophilic sponge as the sponge prophy shown in FIG. 2 is applied to the curved surface of the neck of a tooth without damaging the gums as shown in FIG. 5, in which the teeth contact surface of core 1 is curved. The effect of this embodiment is similar to that of the conventional cup-shaped prophy chip. In the embodiment cleaning embrasures between the teeth, the conical sponge prophy as shown in FIG. 3 is applied to confining sites such as the embrasures between teeth as shown in FIG. 6, in which core 1 has a conical top suitable for the embrasures. This embodiment prevents chopping of the sharpened and thin top of the conventional silicon gum.

Figure 7:
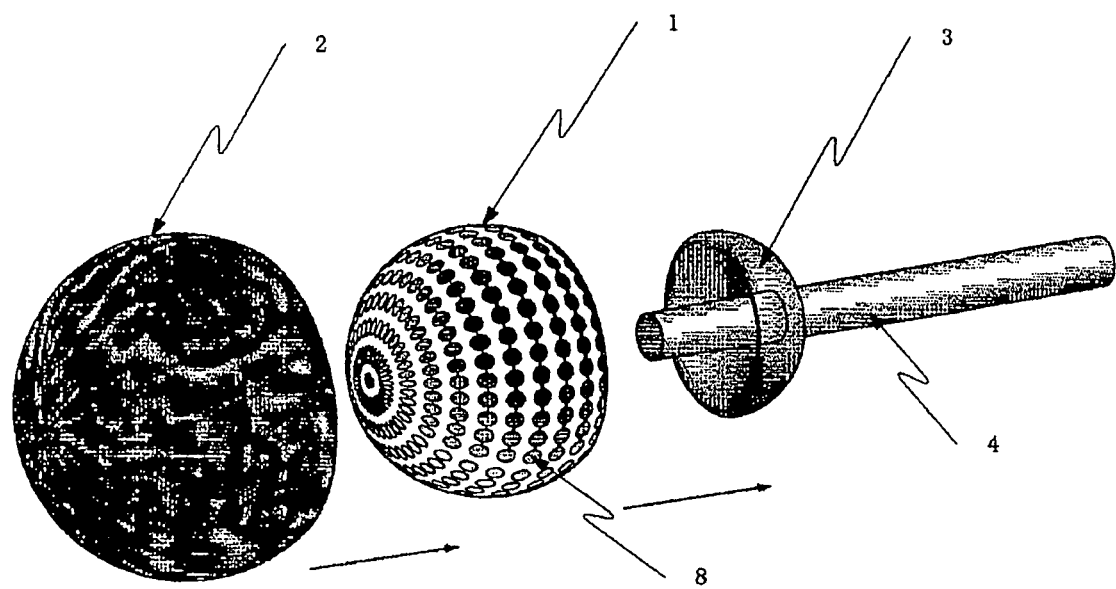
FIG. 7 is an exploded view of a sponge prophy in an embodiment of the invention, showing a plurality of pores in the sponge prophy transferring agents therethrough.
Figure 9:
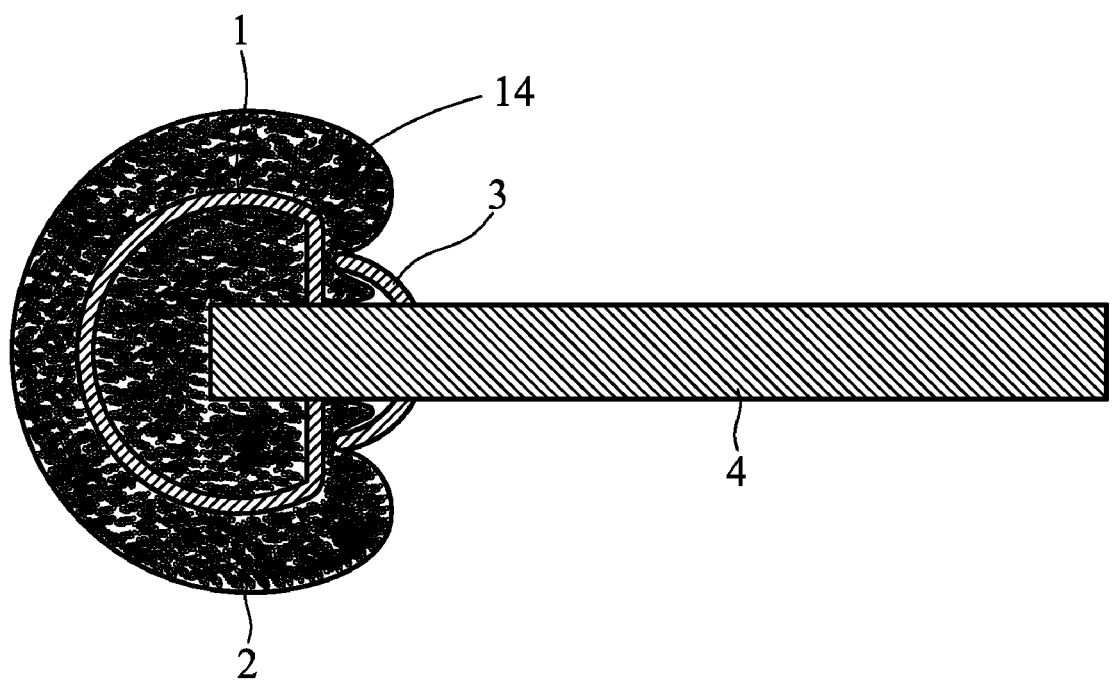
FIG. 9 is a cross-section of a sponge prophy in another embodiment of the invention.

In addition, the hollow portion of core 1 as shown in FIG. 7 can be filled with agents such as various medicaments, a sweetener, a fragrance, or a coating agent. Hydrophilic grindstone sponge 2 is immersed in water prior to the operation, and the agents can be dissolved and released through pores 8 to the surface of hydrophilic grindstone sponge 2, providing various medical or aromatherapeutic effects. In the embodiment shown in FIG. 9, the hollow portion of core 1 is filled with a water-retaining material 14, providing dissipation of heat generated by friction, and prolonging the effect of the foaming agent, the sweetener, the fragrance, the medicament for preventing periodontal diseases and dental caries, or the coating agent since the amount of these agents is increased.

It is to be noted that the shapes of the sponge prophy or latch plate 3, or the fixation are not confined by the illustrated examples. While the invention has been described by way of example and in terms of preferred embodiment, it is to be understood that the invention is not limited thereto. All shapes of the core other than those shown in FIGS. 1~3 are applicable.

What is claimed is:

1. A dental cleaning device, comprising:
 a rotary dental instrument comprising a switch; and
 a prophy chip comprising:
  a cup-shaped core with semispherical canopy, cylindrical, cupped, conical, inverted conical, or disk profile, the core comprising an exterior wall and a hollow interior region;
  a shaft containing a connecting means for connecting the prophy chip to the dental rotary instrument to avoid vibration around a rotation axis of the core during rotation;
  a hydrophilic grindstone sponge covering the exterior wall of the core, wherein the hydrophilic grindstone sponge comprises a grindstone therein; and
  a latch plate fixing the hydrophilic grindstone sponge to the core;
 wherein the prophy chip is mounted on a top of the dental rotary instrument for cleaning, polishing, and burnishing teeth, and the hydrophilic grindstone sponge is immersed in water prior to operation or absorbed saliva during operation without using a polishing paste to dissipate heat generated by friction, and wherein the switch is configured to activate the dental rotary instrument to drive rotation of the prophy chip.

2. The dental cleaning device as claimed in claim 1, wherein the hydrophilic grindstone sponge is hydrophilic latex sponge, or polyurethane sponge, and the hydrophilic latex sponge or the hydrophilic polyurethane sponge comprises a grindstone of $Ca_{10}(PO_4)_6(OH)_2$ or $Ca_{10}(PO_4)_6F_2$ as a wet grindstone sponge covering the core.

3. The dental cleaning device as claimed in claims 1 or 2, wherein the hydrophilic grindstone sponge further comprises at least one water soluble agent consisting of a foaming agent, a sweetener, a fragrance, a medicament for inhibiting or preventing periodontal diseases or dental caries, or a coating agent.

4. The dental cleaning device as claimed in claims 1 or 2, wherein the exterior wall of the core is reticular or porous and at least one water soluble agent consisting of a foaming agent, a sweetener, a fragrance, a medicament for inhibiting or preventing periodontal diseases or dental caries is disposed in a hollow interior region of the core.

5. The dental cleaning device as claimed in claim 1, wherein an outside of the core is nonwoven to maintain the hydrophilic grindstone sponge and has hydrophilicity and flexibility.

6. The dental cleaning device as claimed in claim 1, wherein an outside of the hydrophilic grindstone sponge covering the core is a three-dimensionally continuous, porous film for conducting a solution from a flexible polishing agent.

7. The dental cleaning device as claimed in claim 1, wherein a coating agent is disposed in the hollow interior region of the core.

8. The dental cleaning device as claimed in claim 1, wherein the core is filled with a water-retaining material immersed in a water soluble agent, wherein the water soluble agent is releasable from a surface of the hydrophilic grindstone sponge covering the core.

9. The dental cleaning device as claimed in claim 1, wherein the hydrophilic grindstone sponge is folded over an edge of the wall into the hollow interior region of the core and gripped by the latch plate.

10. The dental cleaning device as claimed in claim 1, wherein the core is directly connected to the shaft.

* * * * *